(12) United States Patent
Bodor et al.

(10) Patent No.: US 6,849,281 B2
(45) Date of Patent: Feb. 1, 2005

(54) FOOD PRODUCT SUITABLE FOR REDUCING LOW DENSITY LIPOPROTEIN CHOLESTEROL LEVELS

(75) Inventors: Janos Bodor, Vlaardingen (NL); Gijsbertus Johannes Van Oorschot, Vlaardingen (NL); Mario Jorge Santos Da Silvo, Vlaardingen (NL); Eelko Gerben Ter Schure, Vlaardingen (NL); Elke A. Trautwein, Vlaardingen (NL)

(73) Assignee: Unilever Bestfoods, North America, a division of Conopco, Inc., Englewood Cliffs, NJ (US)

(*) Notice: Subject to any disclaimer, the term of this patent is extended or adjusted under 35 U.S.C. 154(b) by 0 days.

(21) Appl. No.: 10/072,580

(22) Filed: Feb. 8, 2002

(65) Prior Publication Data

US 2003/0104004 A1 Jun. 5, 2003

(30) Foreign Application Priority Data

Feb. 9, 2001 (EP) ............................................. 01200489
Feb. 9, 2001 (EP) ............................................. 01200493

(51) Int. Cl.⁷ ......................... A23L 1/20; A61K 31/352; C12P 1/02; C12N 1/14
(52) U.S. Cl. ........................... 426/46; 426/61; 435/171; 435/254.1; 514/456
(58) Field of Search .................... 426/46, 61; 435/171; 435/254.1; 514/456, 460

(56) References Cited

FOREIGN PATENT DOCUMENTS

| EP | 0 556 699 | | 8/1993 |
| GB | 2 046 737 | | 11/1980 |
| WO | 97/31546 | * | 9/1997 |
| WO | 99/23996 | | 5/1999 |
| WO | 00/30665 | | 6/2000 |
| WO | 00/64276 | | 11/2000 |

OTHER PUBLICATIONS

Wang et al., Life Sciences, 65/25, pp. 2663–2877 (Nov. 12, 1999) (abstract).*
United States Food And Drug Administration (FDA), Docket No. 97–0441, Final Decision (May 20, 1998).
United States Food And Drug Administration (FDA) titled: "Reference Amounts Customarily Consumed Per Eating Occasion" (1999).
"Reduction Of The Cholesterol Content Of Eggs By The Oral Administration Of Lovastatin To Laying Hens", R. Elkin and J. Rogler; *Journal of Agriculture and Food Chemistry*; 38 (1990), Aug., No. 8, Washington D.C.
"Meta–Analysis Of The Effects Of Soy Protein Intake On Serum Lipids"; J. Anderson et al.; *The New England Journal Of Medicine*; Aug. 3, 1995, pp. 276–282.
"*Monascus Purpureus*–Fermentated Rice (Red Yeast Rice): A Natural Food Product That Lowers Blood Cholesterol In Animal Models Of Hypercholesterolemia"; Li et al.; *Nutrition Research*; vol. 18, No. 1, pp. 71–81, 1998.
"Cholesterol–Lowering Effects Of A Proprietary Chinese Red–Yeast–Rice Dietary Supplement"; Heber et al.; *American Journal of Clinical Nutrition*; 1999; 69; pp. 231–236.
XP–002203259: "Evaluation Of Genistin and Genistein Contents In Soybean Varieties And Soy Protein Concentrates Prepared With 3 Basic Methods" (abstract) Pandjaitan et al., Journal Food Science (Apr. 2000).
XP–002203260: "Preventive Effect Of Dietary Fermented Soybean On Bone Loss In Ovariectomized Rats: Enhancement With Isoflavone And Zinc Supplementation" (abstract) Zhong et al., J. Health Sci. (2000).

* cited by examiner

*Primary Examiner*—Phyllis Spivack
(74) *Attorney, Agent, or Firm*—Gerard J. McGowan, Jr.

(57) ABSTRACT

A food product suitable for reducing low density lipoprotein cholesterol levels comprising an amount of soy protein of at least 5 grams per average serving and at least 5 mg/kg statins is described. Preferably the food product comprises a fermented soy ingredient.

8 Claims, No Drawings

FOOD PRODUCT SUITABLE FOR REDUCING LOW DENSITY LIPOPROTEIN CHOLESTEROL LEVELS

TECHNICAL FIELD

The present invention relates to food products suitable for reducing low density lipoprotein cholesterol levels in the human blood.

BACKGROUND OF THE INVENTION

Cardiovascular disease is a leading cause of morbidity and mortality, particularly in the United States and in Western European countries and is emerging in developing countries. Several factors are mentioned relation to the development of cardiovascular disease including hereditary predisposition to the disease, gender, lifestyle factors such as smoking and diet, age, hypertension, and hyperlipidemia, including hypercholesteremia. Several of these factors, particularly hyperlipidemia and hypercholesteremia, contribute to the development of atherosclerosis, a primary cause of vascular and heart disease.

Elevated low-density lipoprotein cholesterol (hereafter "LDL-cholesterol") is directly related to an increased risk of coronary heart disease.

The presence of soy protein in food consumed by humans is associated with a lower level of low-density lipoprotein cholesterol (LDL-cholesterol) and lower risk of coronary heart disease.

Food products comprising soy protein are well known. Examples of food products that may comprise soy protein are meat products, baked products, food analogs and dairy products. Types of soy proteins and food uses of soy proteins are described in Waggle, D. H. and Kolar, C. W., Soy protein and human nutrition, proceedings of a symposium held May 222–25, 1978 in Keystone Colourado, pages 19–51.

Soy protein materials are known to reduce total cholesterol and LDL-cholesterol levels in the blood of animals. An analysis of the effects of soy protein intake on serum lipids in humans has shown that dietary soy protein is significantly related to lowering serum concentrations of total cholesterol and LDL-cholesterol in humans (Anderson, Johnstone, and Cook-Newell, N. Engl. J. Med., Vol. 333, No. 5, pp. 276–82 (1995)).

Statins are compounds that are known to have a lowering effect on levels of LDL-cholesterol in the human blood. Statins inhibit the hydroxymethylglutaryl coenzyme A (HMG-CoA) reductase, the rate-determining step in the cholesterol biosynthesis.

Scientific research has confirmed the healthy properties of statins especially with respect to LDL blood-cholesterol and triglyceride levels lowering activities, both in animals and in humans (Li et al., Nutrition Research 18, 71–81 (1998); Heber et al., Am. J. Clin. Nutr. 69, 231–236 (1999)).

Early reports of the effect of statins were made in 1979. The Japanese scientist Endo isolated a metabolite from *Monascus* that reduced artificially induced hyperlipoproteinemia in rats (Endo, J. Antibiotics 32, 852–854, (1979)). These metabolites are known as monacolins. Monacolin is identical to the cholesterol lowering pharmaceutical lovastatin. Lovastatin is sold by Merck co. under the tradename Mevacor. A derivative of lovastatin, simvastatin, is sold as a cholesterol-lowering drug under the name of Zocor. Other derivatives of lovastatin e.g. pravastatin, and mevastatin, are also sold as lipid lowering drugs against hypercholesterolemia. *Monascus*-extracts are sold in capsules in Japan as the dietary product Monacolin. The usual dose of the above statins is 20 mg/day, which results in at least 20% blood LDL-cholesterol lowering.

The production of statins is also reported in fermentation using fungi other than the above-mentioned *Monascus* species. It has been shown that statins can be produced by a variety of filamentous fungi, including *Monascus, Aspergillus, Penicillium, Pleurotus, Pythium, Hypomyces, Paelicilomyces, Eupenicillium,* and *Doratomyces.*

The preparation and purification of the statins used in pharmaceutical preparations involves many process-steps, in which ingredients are used that are not commonly used in the food industry. The many process steps increase costs compared to processes having less process steps. For these reasons the statins prepared for pharmaceutical use are not used in the foods industry.

As a food product, rice fermented with a red *Monascus* fungus (red rice) has been known and used for hundreds of years in China. Red rice was used and still is used in wine making, as a food-colouring agent and as drug in traditional Chinese medicine. We have found that most red rice available on the market contains no statins or statins in very low amounts. The Food and Drug Administration has concluded that red yeast rice available in the market does not contain significant amounts of lovastatin (FDA, Docket No. 97-0441, Final Decision).

WO 99/23996 describes a composition for treating elevated serum cholesterol and/or triglycerides comprising a red rice product containing at least 0.05% lovastatin by weight.

Red rice powder capsules are sold as dietary supplements under the name of Cholestin by the firm Pharmanex. Pharmanex also sells a Cholestin bar containing red yeast rice (*Monascus purperus went*).

Red rice has an intensive red color. Whereas the intensive red colour of red rice is an advantage when it is used as colouring agent, it is a disadvantage when it is used in the majority of food products. Due to the intense red colour of red-rice products, the foods prepared from red rice are coloured, depending on the amount of red-rice product added to the food product yellow, orange or red. The higher the amount of red rice added to the food, the more intense is the red colour of the food product. In the known food products a relatively large amount of red rice has to be added in order to add enough statins. This results in a red color of the products that cannot be avoided.

In some food products the red rice coloring is undesirable. In particular in the western world, consumers are reluctant to use products of which the color has changed from that they are used to. For example spreads, including margarine, butter, low fat spreads and cooking or salad oils are considered unacceptable by customers when the colour of such a product is intense yellow or orange or red. However, at the same time these type of products have been found by the applicant to be excellent vehicles of the daily intake of amounts of statins sufficient to obtain a blood LDL-cholesterol lowering effect.

SUMMARY OF THE INVENTION

It is an object of the invention to provide a food product that has no undesired colouring due to the addition of statins. A further object of the invention is to increase the health effects of the known food products comprising statin. Another, object is to provide a process for the preparation of a food product comprising statin, which involves less process steps than in the preparation of statins as a pharmaceutical drug. Another object is to provide such a process, which avoids the use of ingredients or process aids that are not commonly used in the food industry. One or more of these objects are attained by the invention.

We have now found a food product comprising an amount of soy protein of at least 5 grams per average serving, characterized in that the food product comprises at least 5 mg/kg statins.

Advantageously the food product comprises a fermented soy ingredient.

Surprisingly we have found that when the substrate for the *Monascus* fermentation is soybeans and/or soybean ingredients, the red coloring of the fermented product as in red rice fermentation is avoided, i.e. a non-coloured or only slightly coloured fermentation product is obtained. Further we have found that compounds having a positive health effect, which are present in soybeans are also present in the fermented product. These compounds include, but are not limited to polyunsaturated fatty acids, phytosterols, dietary fibers including soluble fibers, polyphenols and saponins. As a result of the presence of these compounds in the fermentation product, the food product according to the invention has increased health effects compared to the known food products comprising statin.

DETAILED DESCRIPTION OF THE INVENTION

The following definitions will be used.

Statins are defined as substances having the structural formula, presented in formula (1).

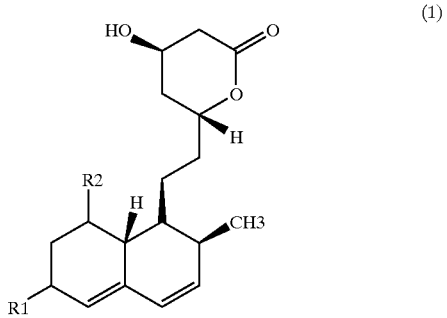

(1)

In this structural formula, R1 and R2 can be any group. Preferred statins are those that are given in table 1.

TABLE 1

| Preferred statins according to formula (1) | | |
|---|---|---|
| | R1 | R2 |
| monakolin K | CH3 | CH3—CH2—CH(CH3)—C(=O)—O— |
| monakolin L | CH3 | H |
| monakolin J | CH3 | OH |

TABLE 1-continued

| Preferred statins according to formula (1) | | |
|---|---|---|
| | R1 | R2 |
| monakolin X | CH3 | CH3—C(=O)—CH(CH3)—C(=O)—O— |
| monakolin M | CH3 | CH3—CH(OH)—CH(CH3)—C(=O)—O— |
| compactin (ML-236B) | H | CH3—CH2—CH(CH3)—C(=O)—O— |
| ML-236-A | H | OH |
| NL-236-C | H | H |

Polyphenols herein are polyphenols having plant origin. These include flavenoids, which include isoflavones. The polyphenols include isoflavones, stilbenes, lignans, coumestans and resorcyclic acid lactones. Examples of isoflavones are genistein daidzein, equol, glycitein, biochanin A, coumestrol, maitaresinol, formononetin, O-desmethylengolesin, enterolactone and enterodiol. Preferred isoflavones according to the invention are genistein and daidzein and glycitein, which are present in soybeans.

Saponins are herein derived as β-D-glucopyranosiduronic acid derivates. Examples of saponins are Soya sapogenol A, B, C, D and E, Soyasaponin I, II and III, as described in Lebensmittel Lexikon, B. Behr's Verlag GmbH & Co. Hamburg, Bd. 2, L–Z -3, 1993, pages 550–552.

Polyunsaturated fatty acid esters are defined as fatty acid esters having more than one unsaturated group in the fatty acid chain. Examples of polyunsaturated fatty acid esters are linoleic acid esters, linolenic acid esters, arachidonic acid esters.

Dietary fibers are herein a collective term for a variety of plant substances, that are resistant to digestion by the human gastrointestinal enzymes. Depending on their solubility, dietary fibers can be classified into insoluble (cellulose, some hemicelluloses, lignins), and soluble (remainder of the hemicelluloses, gums, mucilages. Soybean colyedon fibers comprise both soluble and insoluble dietary fibers.

Phytosterols are herein defined as sterol compounds produced by plants, which are structually very similar to cholesterol except that they contain some substitutions at the C24 position on the sterol side chain. The phytosterols include 4desmethylsterols, 4-monomethylsterols, 4,4'-dimethylsterols and mixtures thereof. Examples of such phytosterols are β-sitosterol, campesterol, stigmasterol. The term phytosterols herein also includes phytostanols, the saturated equivalents of phytosterols.

Polyphenols, polyunsaturated fatty acids, phytosterols, proteins, peptides, dietary fibers, and saponins will hereinafter collectively be referred to as soy actives.

Unless otherwise indicated, the amounts given will be expressed, in wt. % or weight parts per million (ppm), mg/kg or g/kg, relative to the total weight of the food product, unless otherwise indicated.

The amounts of statins given herein are the sum of the amounts of individual statins, as e.g. determined by chromatography, unless otherwise indicated.

The substrate is herein defined as total of compounds in the fermentation medium, without the solvent, for instance without water, in case a waterbased fermentation medium is used. In case no solvent is present the substrate equals the fermentation medium.

The protein amounts given herein are the sum of the amounts of individual proteins, unless otherwise indicated.

The amounts of soy actives are expressed as the sum (wt. % or ppm) of polyunsaturated fatty acids, phytosterols, proteins, peptides, dietary fibers including soluble fibers, polyphenols and saponins.

Food products according to the invention are preferably foods in which soy protein materials are used as functional ingredients.

They include, but are not limited to, meats such as ground meats, emulsified meats, fermented meats and marinated meats, beverages such as nutritional beverages, sports beverages, protein fortified beverages, juices, milk, milk alternatives, and weight loss beverages, cheeses and cheese like products, such as tofu, frozen desserts such as ice cream, ice milk, low fat frozen desserts, and non-dairy frozen desserts, yoghurts, soups, sauces, such as soy sauce, puddings, breakfast cereals, pasta products, bakery products, such as bread and cake, salad dressings, and dips and spreads such as mayonnaise, chip dips, low fat spreads, sandwich spreads, dietetic products e.g. slimming products or meal replacers etc.

Preferably a food product according to the invention does not include products especially suitable for the feeding of animals (feed).

The statins and soy proteins are present in the food product in an amount sufficient to obtain a blood LDL-cholesterol lowering effect if the food product is used according to the common needs of the consumer.

The skilled person will be able to adjust the percentage of statins and soy proteins in the food product to get the above effect. The percentages will depend on the type of food product, since the food products are used in different serving sizes. Moreover the pattern in a food product is consumed (servings per day and distribution over days) is dependent on the food product. Data about serving sizes may be found in the list published by the United States Food and Drug Administration (FDA) titled: "Reference Amounts customarily consumed per eating occasion".

As an illustration, table 2 indicates a number of products, which may be prepared according to the invention, and a typical serving size.

TABLE 2

| Product | Average serving (grams) |
|---|---|
| Margarine | 15 |
| Meat product | 50 |
| Bar | 60 |
| Meal replacer drink | 330 |
| Yoghurt type drink | 200 |
| Ice cream | 75 |
| Cereal | 50 |
| Beverage | 200 |

Preferably the food product according to the invention comprises non-glycosylated isoflavone. In soy beans and soy materials derived from soy, isoflavones are present substantially in the glycosylated form. Typically about 5 wt. % of the isoflavones is resent in the non-glycosylated form. The most important glycosylated isoflavones are genistin, daidzin and glycetin. The non-glycosylated forms are respectively genistein, daidzein and glycetein. Genistein, daidzein and glycetein have been reported to have advantageous health effects, including estrogenic and antioxidant properties.

We have found that due to the fermentation according to the invention the glycosylated isoflavones are converted into the corresponding non-glycosylated isoflavones, which are more benificial. For instance, the amount of genistein and daidzein is increased in the fermented soy compared to the non-fermented soy. Surprisingly this advantageous conversion occurs simultaneously with the production of statin.

The invention therefore further relates to a food product comprising statin, soy protein, genistein and genistin, wherein the amount of statin is 5–500 mg/kg, the amount of soy protein is 10–500 g/kg and the amount of genistein is 10–99 wt. %, preferably 15–99 wt. %, more preferably 20–95 wt. %, still more preferably 20–90 wt. %, most preferably 20–80 wt. % of the sum of the amounts of genistein and genistin.

The invention further relates to a food product comprising statin, soy protein, daidzein and daidzin, wherein the amount of statin is 5–500 mg/kg, the amount of soy protein is 10–500 g/kg, and the amount of daidzein is 10–99 wt. %, preferably 15–99 wt. %, more preferably 20–95 wt. %, still more preferably 20–90 wt. %, most preferably 20–80 wt. % of the sum of the amounts of daidzein and daidzin.

The absolute amounts of genistein and daidzein may, for each food product, be adjusted by the skilled person to a desired level. This may for instance be done by selection of the soy material to be fermented from materials having a different isoflavone content, by adjustment of the fermentation conditions, such as fermentation time, and by selecting the amount of fermented soy added to the food product. In such way the amount may be adjusted to a desired daily intake of the isoflavones, that could be for instance 50–80 mg/day for genistein. The preferred absolute level of genistein in the food products according to the invention, depends on the food type, and may be 50 mg/kg or more, more preferably 100 mg/kg or more, 200 mg/kg or more, 500 mg/kg or more and most preferably 200–5000 mg/kg. Also the absolute level of daidzein depends on the food type, and may be 50 mg/kg or more, more preferably 100 mg/kg or more, 200 mg/kg or more, 500 mg/kg or more and most preferably 200–5000 mg/kg.

Preferably the food product according to the invention is a spread, meat product, bakery good, breakfast cereal, beverage or bar. These products are preferred because the way in which they are consumed results in a more controlled and constant intake of statins and soy proteins than in other food products. More preferred food products according to the invention are a spread, bar, or beverage.

The invention will now be further illustrated by the description of suitable embodiments of the more preferred food products. It belongs to the ability of the skilled person to use the teaching provided therewith to prepare other products of the invention.

Meat Products

Meat products according to the invention usually have a composition of known meat products, however part of the protein in the meat product is soy protein comprising statin. Examples of types of meat products are hamburgers, sausages, such as fermented sausages, cooked sausages, such as frankfurter type sausages, pate, etc.

An example composition of a fermented sausage is: minced meat 40–70 wt. %, mycoprotein 0–25 wt. %, 5–30 wt % fermented soy protein comprising statin, 0.1–1 wt. % sodium caseinate, 0.1–1 wt. % transglutaminase, nitrite salt 0.5–5 wt. %, glucose 0.1–1 wt. %, *Pediococcus* culture mix 0.001–0.010 wt. % and 0–1 wt % flavouring, salt, etc.

An example composition of a frankfurter type sausage is: 10–40 wt. % minced pork meat, 5–20 wt. % minced beef meat, 5–25 wt. % fermented soy protein comprising statin, 0–3 wt. % salt, 0–2 wt. % nitrite, 0–3 wt. % phosphate, 20–50 wt. % water.

A typical size for a meat product could be from 20 to 200 g, generally from 40 to 100 g. Preferred levels of statins and protein in such products are: 15–350 mg/kg statin and 30–300 g/kg soy proteins. More preferred ranges for these levels are 50 to 200 mg/kg statin and and 50–400 g/kg soy proteins respectively.

Beverages

Preferred food products according to the invention are beverages, for example tea, fruit juice, soft drinks, meal-replacer drinks, etc.

The beverage may be a beverage which is ready to drink or a powdered beverage, to which water has to be added to prepare a ready to drink beverage.

Meal replacer drinks will be described in more detail herein below. It will be apparent that similar levels and compositions apply to other beverages comprising statins and soy proteins. A typical serving size of a beverage is taken to be 200 ml.

Meal replacer drinks are typically based on a liquid base, which may for example be thickened by means of gums or fibres and whereto a cocktails of minerals and vitamins are added. The drink can be flavoured to the desired taste e.g. fruit or chocolate flavour. A typical serving size may be 330 ml or 330 grams.

An example composition for a meal replacer beverage is about 70–85 wt. % water, 2–10 wt. % soy protein comprising statins, 5–15 wt. % sugar (e.g. sucrose), 0–4 wt % fat, 0.1–1 wt. % vitamins and minerals, 0.01–2 wt. % flavour, 0.1–0.5 wt. % thickener.

Preferred levels of statins and protein in a beverage are: 20–100 mg/kg statin and 20–80 g/kg soy proteins. More preferred ranges for these levels are 30 to 70 mg/kg statin and and 30–50 g/kg soy proteins respectively.

Food Bars, Including Cereal Bars

These products often comprise a matrix of edible material wherein the statin and soy proteins can be incorporated. For example the matrix may be fat based (e.g. couverture or chocolate) or may be based on bakery products (bread, dough, cookies etc). Preferably the food product is a cereal bar, in which the matrix is based on agglomerated cereal particles (rice, grain, nuts, raisins, fruit particles).

The matrix material of a bar may be present in an amount of 60–95 wt. % of the weight of the bar, preferably 70–90 wt. % most preferred 75–85 wt. %. The matrix material may contain 5–30 wt. % soy ingredient comprising statin, preferably 10–25 wt. %, more preferably 15–25 wt. %, based on total weight of the food bar.

Other ingredients in the cereal bar may be starch, sugar (e.g. 0–10 wt. %), sirups, honey, water, milk solids (0–10 wt. %), salt (e.g. 0–5 wt. %) calcium carbonate (e.g. 0–5 wt. %), vitamins, flavouring and colouring.

The ingredients are usually mixed and cooked (e.g. by cooking-extruding), formed to the desired shape and size, to produce the (cereal) bar.

A typical size for a food bar could be from 20 to 100 g, generally from 40 to 60 g. Preferred levels of statins and protein in food bar are: 50–500 mg/kg statin and 50–300 g/kg soy proteins. More preferred ranges for these levels are 100 to 350 mg/kg statin and and 80–250 g/kg soy proteins respectively.

Dairy Type Products

Examples of dairy products according to the invention are dairy spreads, cream cheese, milk type drinks and yoghurt, where the milk solids are partly or fully replaced by fermented soy ingredient, preferable fermented soy protein isolate.

An example of a composition for a yoghurt type product is about 50–80 wt. % water, 3–12 wt. % soy protein comprising statins, 0–15 wt. % whey powder, 0–15 wt. % sugar (e.g. sucrose), 0.01–1 wt. % yoghurt culture, 0–15 wt. % fruit, 0.05–0.5 wt. % vitamins and minerals, 0–2 wt. % flavour, 0–5 wt. % stabilizer (thickener or gelling agent).

A typical serving size for a yoghurt type product could be from 125 to 250 g, generally from 150 to 225 g. Preferred levels of statins and soy protein in the yoghurt type product are: 40–200 mg/kg statin and 20–100 g/kg soy proteins. More preferred ranges for these levels are 40 to 80 mg/kg statin and and 30–60 g/kg soy proteins respectively.

Frozen Confectionery Products

For the purpose of the invention the term frozen confectionery product includes milk containing frozen confections such as ice-cream, frozen yoghurt, sherbet, sorbet, ice milk and frozen custard, water-ices, granitas and frozen fruit purees.

Preferably the level of solids in the frozen confection (e.g. sugar, fat, flavouring etc) is more than 3 wt. %, more preferred from 10 to 70 wt. %, for example 40 to 70 wt. %.

Ice-cream will typically comprise 2 to 20 wt. % of fat, 2 to 20 wt. % of soy ingredient comprising statin, sweeteners, 0 to 10 wt. % of non-fat milk components and optional components such as emulsifiers, stabilisers, preservatives, flavouring ingredients, vitamins, minerals, etc, the balance being water. Typically ice-cream will be aerated e.g. to an overrun of 20 to 400%, more specific 40 to 200% and frozen to a temperature of from −2 to −200° C., more specific −10 to −30° C. Ice-cream normally comprises calcium at a level of about 0.1 wt %.

Other food product according to the invention can be prepared by the skilled person based on common general knowledge, using soy protein comprising statin as an ingredient in suitable amounts. Examples of such food products are baked goods, dairy type foods, snacks (e.g. roasted soynuts), etc.

Preparation of the Food Product

According to the invention a substrate, prepared from soybeans and/or ingredients thereof, such as defatted soy, soy protein concentrate or isolate, textured soy protein, etc. is fermented with a filamentous fungus and the fermentation product is used in the preparation of a food product. These steps will be illustrated below. In this illustration the filamentous fungus is a *Monascus* fungus.

Fermentation is conducted in known way. The fermentation is conducted in at least one fermentation vessel (fermenter) in which a medium comprising soybeans and/or ingredients thereof is present. The fermentation is started (inoculated) by adding a suspension of spores of the *Monascus* fungus (inoculum), which has been prepared by fermenting *Monascus* fungus on a separate medium. The fermentation may be executed batchwise or as a continuous process.

The fermentation involves the following steps, which are executed in the given order:
a) Preparation of the medium for the inoculum and the medium to be used in the fermenter
b) Sterilization of the media, fermenters and ancillary equipment c) Production of inoculum
d) Addition of the inoculum to the medium comprising soybeans and/or ingredients thereof, in the fermenter.
e) Conducting the fermentation
f) Removal of the fermentation product from the fermenter The fermentation product is used in the preparation of the food products according to the invention.

Optionally, before the fermentation product is used in the preparation of the food products, the following additional process steps may be executed:
g) Sterilization of the fermentation product
h) Drying of the fermentation product (or sterilized fermentation product)
i) One or more separation steps, for instance extraction, to separate statins and soy actives from *Monascus* biomass in the fermentation product The medium used in the fermenter may be solid or liquid. Advantageously the medium is solid, most preferred the medium substantially consists of crushed whole soybeans, which have been soaked with water until the moisture content reaches 20–35 wt. % water). In case the medium is liquid, usually water is present as major constituent of the medium.

Whole soybean are preferably used as a medium for the fermentation. Typical composition of whole soybeans is 42% wt. % protein, 20 wt. % oil, 35% wt. % total carbohydrates, 5 wt. % ash and 5.5 wt. % crude fiber (Kawamura, S., Tech. Bull. Faculty Agric., Kagawa Univ., 18, 117 (1967)).

Instead of whole soybeans, parts or ingredients of soybean may be used in the medium for the fermenter, for instance soy protein (including textured vegetable protein), soy milk, soy-flakes etc. Care has to be taken that the medium contains compounds that can provide a carbon source and a nitrogen source for growth of the *Monascus* fungus.

The *Monascus* fungus used according to the invention may be any *Monascus* fungus that produces statins. Preferably the fungus is chosen from the group of *Monascus ruber* Most preferred is *Monascus ruber* F125 M1-4.

Strains F125 and F125 M1-4 are deposited at the Centraal Bureau voor Schimmelculturen (CBS) as no. CBS 109070 on 14.11.2000 and no. CBS 109269 on 23.01.2001.

These deposits were made under the provisions of the Budapest Treaty on the International Recognition of the Deposit of Microorganisms for the Purpose of Patent Procedure and the Regulations thereunder (Budapest Treaty).

Availability of the deposited material is not to be construed as a license to practice the invention in contravention of the rights granted under the authority of any government in accordance with its patent laws.

The medium will ordinarily be sterilized before fermentation, e.g. by heat treatment, like pasteurization.

The medium in the fermenter may contain other substances, which may aid the fermentation, for instance sugars, amino acids and vitamins.

The fermentation may be carried out in a manner, which can be determined by the skilled person on the basis of common general knowledge of fermentation technology. As illustration preferred embodiments are described hereunder.

The fermentation temperature may be important. The temperature is preferably in the range of 10 to 37° C. more preferably 20 to 30° C. We have found that at 37° C. and higher the production of statins decreases.

Preferably during fermentation the medium is aerated, e.g. by stirring, shaking etc. Aeration may be carried out by blowing air through the fermentation medium. Preferably the air is wholly or partly saturated with water vapour in case solid state fermentation is used. This avoids drying out of the fermentation medium.

The relative levels of statins to soy actives will depend on the fermentation time. The fermentation time is therefore dependent on the desired amount of statins in the fermentation product. Preferred fermentation time is 1–60 days, more preferably 1–50 days, still more preferably 15–40 most preferably 20–30 days.

Prior to addition to the food product, the fermentation product may be subjected to a separation step, to separate statins and soy actives from *Monascus* biomass in the fermentation product. This separation may be done with known separation techniques, e.g. filtration or centrifugation.

The fermentation product may also be extracted and the extract may be used in the preparation of the food product.

The extraction may be done on the fermentation product. Alternatively the *Monascus* biomass may be separated from the fermentation product prior to extraction, e.g. by filtration. The *Monascus* biomass may be separately extracted and the resulting extract can also be used in the preparation of the food product.

Extracts may be used as such in the preparation of food products. Preferably extraction solvent may be removed from the extracts, e.g. by evaporation of the extraction solvent. Alternatively the fermentation product may be diluted, e.g. by adding soy ingredients.

Advantageously a vegetable oil may be used as extractant. When the fermentation product is extracted with vegetable oil, such as for instance soybean oil, it was found that the statin is effectively extracted and an oil phase containing substantially all statin is obtained. The resulting extract, i.e. vegetable oil is very suitable to be used directly as a food ingredient.

Most advantageously the extractant, e.g. vegetable oil is added to the fermentation medium during fermentation. We have found that in the presence of an extractant, the production of statins during fermentation is considerably increased. It is possible to increase the amount of statin produced by at least a factor 10, more preferably at least a factor 40, compared to a fermentation without extractant, by the addition of vegetable oil during the fermentation. Preferably the extractant should not interfere with the fermentation, especially it should not be poisonous for the filamentous fungi.

The fermentation product (including extracts etc.) may directly be added to food product ingredients in the process of preparation of the food products according to the invention. It, however may be required that the fermented product is pasteurized, dried, etc. in order to preserve or modify it before it is further used for the preparation of a food product. It can be added to the other ingredients of the food product composition, or it may be added to part of the ingredients, before other ingredients are added. If more than one phase is present in the food product the fermentation product may be present in one or more of these phases. Preferably the fermentation product will substantially be present in an oil phase, if such oil phase is present.

Soy protein content in a food product according to the invention may be measured according to the method described in Agater et al., J. Sci. Food Agric. (1986), 37(3), 317–31.

The invention will be further illustrated in the examples.

EXAMPLES

Example 1

A. Preparation of *Monascus* Strain F125 M1-4

*Monascus ruber* strain F125 was cultivated in malt water liquid medium at 30° C. for 4 days. Of this culture, 1 ml was used as an inoculum for a Hybond-N filter (Amersham, UK) placed on a YE plate (4% glucose, 0.3% $KH_2PO_4$, 1.0% yeast extract (Difco), 1.5% agar). After 3 days incubation at 30° C., the spores were harvested by washing the filters with 10 ml physiological saline containing 0.1% Tween 80. The spores were filtered 4 times through Mira cloth filters to obtain a hyphae free spore suspension. This suspension was used for subsequent mutagenesis.

The spores were diluted to a concentration of $10^8$ spore/ml then exposed to UV light at an intensity of 100 joules/$m^2$. The mutagenised spores were plated on Potato Dextrose Agar (Oxoid) and incubated for 3 weeks. One of the resulting colonies, which had a lighter colour than the others was selected and is herein defined as *Monascus* strain F125 M1-4.

The strain F125 M1-4 was deposited at the Centraal Bureau voor Schimmelculturen (CBS) on 14.11.2000 and has number CBS 109070.

B. Preparation of *Monascus* Spores

*Monascus* f125M1-4 spores were prepared by harvesting *Monascus* mycelium from a PDA (potato dextrose agar) (oxoid) slope by washing with 5 ml physiological saline and incubating the mycelium in 150 ml malt water (oxoid) for 4 days at 30° C. The spores were harvested by filtration through a Mira cloth filter.

C. Fermentation

C.1. Preparation of an Inoculum

A shake flask containing textured vegetable protein (TVP) is inoculated with filamentous spores suspended in a physiological water solution containing 0.1 wt. % Tween 80 (polyoxyethylene sorbitan fatty acid ester, available from ICI Specialty Chemicals™). This shake flask is incubated to let the mould grow. This results in a *Monascus* spore suspension, which was adjusted by dilution to a concentration of $1*10^6$ spores/ml.

C.2. Preparation of Fermentation Medium 1 kg of TVP is soaked in tap water (50° C.) for 30 minutes. After soaking the TVP bits are rinsed with cold tap water. Subsequently 50 g batches of the soaked TVP (35 wt % dry matter) were brought in to 300 ml Erlenmeyer flasks.

C.3. Fermentation

The shake flasks were each inoculated with 1 ml of the prepared *Monascus* spore suspension and incubated for 30 days at 30° C. A sample from the shake flask was taken every week to monitor the statin production.

After fermentation, about 600 g textured Soy protein (moisture content 28%) remained. The fermented soy ingredient was pasteurized for 85° C. for 30 mins, cooled and stored for the preparation of food product.

D. Statin Analysis of Fermentation Product

The fermentation product samples are extracted in a 50 ml tube (Falcon) by adding 6 ml of a mixture of acetonitril, water and phosphoric acid (1:1:0.05, v/v/v) The mixture is blended with an Ultraturrax for 1 min. The mixture was then incubated at room temperature on a rollerbank for over 24 hours. Hereafter the samples were centrifuged and the supernatant liquid used for HPLC analysis. Samples were separated using HPLC analysis on a Shimadzu apparatus according to the method of Morovjan et al., J. chromatogr. A 763 (1997) 165–172. The system consists of the Shimadzu SCL-10A system controller, CTO-10AS column oven, LC-10AT vp pump system, RID-10A refraction index detector, SPD-M10A diode array detector and SIL-10AD autoinjector. For the chromatographic determination of statins a Waters NovaPak C18 (150×3.9 mm I.D., 4 µm) column was used operating at 25° C. The eluent was acetonitril-0.1% phosphoric acid (50:50,v/v) solution flowing at 1.5 ml/min. Runs were performed for 15 min. The detection was performed using a diode array detector from 190 nm up to 800 nm. The sum of the area of all peaks in the spectrum belonging to statins is measured. Comparison to a standard (Mevinolin, Sigma) allows the calculation of a statin content (expressed in mg/kg analysed product).

The analysis results in a statin content of 1200 mg/kg.

F. Preparation of a Fermented Sausage

Fermented sausages having the following composition were prepared:

TABLE 4

Composition of fermented sausage

| Ingredient | Wt. % sample a | Wt. % sample b |
|---|---|---|
| Monascus fermented TVP | 10 | 20 |
| Quorn (mycoprotein based meat replacer, ex Marlow foods Limited) | 25 | 15 |
| Salted minced pork | 35.6 | 35.6 |
| Salted bacon | 25 | 25 |
| Na-caseinate | 0.4 | 0.4 |
| Trasglutaminase Active | 0.4 | 0.4 |
| Nitrite salt | 1.96 | 1.96 |
| Sodium ascorbate | 0.06 | 0.06 |
| Glucose | 0.4 | 0.4 |
| Pediococcus starter culture from Quest Int. | 0.016 | 0.016 |
| Water | 0.024 | 0.024 |
| Total | 100 | 100 |

The fermented sausages were prepared by mixing all ingredients. The resulting mixture was fed into sausage casings and the casings were stored for 24 hours at 2° C.

Then, the fermentation of the sausages was executed at 28° C. for about 24 hours, until the pH was 5.2. The resulting sausages were dryed at 20° C. for 4 days. The pH of the sausages was 4.7 and the dry matter content 72 wt. %.

The fermented sausage contained 65 g/kg (sample a), respectively 135 g/kg (sample b) soy protein and 110 mg/kg (sample a), respectively 245 mg/kg (sample b) statins as analysed by the method described hereinbefore.

Example 2

Steps A, B and D. were done according to example 1.

C. Fermentation

C.1. Preparation of an Inoculum

A shake flask containing dehulled soybeans is inoculated with filamentous spores suspended in a physiological water solution containing 0.1 wt % Tween 80 (polyoxyethylene sorbitan fatty acid ester, available from ICI Specialty Chemicals™). This shake flask is incubated to let the mould grow. This results in a *Monascus* spore suspension, which was adjusted by dilution to a concentration of $1*10^6$ spores/ml.

C.2. Preparation of Fermentation Medium 1 kg of dehulled soybeans were soaked in tap water (50° C.) for 30 minutes and subsequently air dried for two hours. Subsequently 50 g batches of the dried dehulled beans were brought in to 300 ml Erlenmeyer flasks.

C.3. Fermentation

The shake flasks were each inoculated with 1 ml of the prepared *Monascus* spore suspension and incubated for 30 days at 30° C. A sample from the shake flask was taken every week to monitor the statin production.

After fermentation, about 600 g soybeans remained. The analysis according to step D results in a statin content of 2800 mg/kg product.

E. Isoflavone Analysis of Fermentation Product

The isoflavone concentration was measured according to the HPLC method described in Franke A. A., et al. (1998): HPLC analysis of isoflavonoids and other phenolic agents from foods and human fluids; *Proceed.Soc.Exp.Biol.Med*; 217 (3), 274–280.

Two samples were tested. The first (comparative) sample was taken from non-fermented fermentation medium, as prepared in step C2 above. The second sample was of equal (solid) weight, but taken from the fermentation product. The results of the isoflavone measurement of these samples are given in table 3.

TABLE 3

Isoflavone concentration in fermented and non-fermented soy

| Isoflavone | Isoflavone concentration (g/kg) | |
|---|---|---|
| | Fermentation medium (unfermented) | Fermentation product |
| Daidzin | 1.107 | 0.304 |
| Genistin | 1.608 | 0.476 |
| Daidzein | 0.057 | 0.9 |
| Genistein | 0.085 | 0.494 |
| Total | 2.9 | 2.2 |

Table 3 shows that the amount of isoflavones in total in the fermentation product is slightly decreased compared to the non-fermented material, but surprisingly the amounts of genistein and daidzein are increased. The fermentation product contains substantial amounts of isoflavones in addition to the statin. The fermentation product had a statin content of 2800 mg/kg, a protein content of 27.8 wt. %, it contained 900 mg/kg daidzein and 494 mg/kg genistein and is suitable as a food ingredient.

What is claimed is:

1. A food product comprising a statin selected from the group consisting of monakolin K, monakolin L, monakolin J, monakolin X, monakolin M, compactin (ML-236B), ML-236-A, and NL-236C, fermented soy protein and genistein and genistin, wherein the amount of statin is 5–500 mg/kg of product, the amount of soy protein is 10–500 g/kg of product and the amount of genistein is 10–99 wt. % of the sum of the amounts of genistein and genistin.

2. The food product according to claim 1, wherein the amount of genistein is 20–80 wt. % of the sum of the amounts of genistein and genistin.

3. The food product according to claim 1, wherein the fermented soy is the product of fermentation of one or more filamentous fungi selected from the group consisting of *Monascus, Aspergillus, Penicillium, Pleurotus, Pythium, Hypomyces, Paelicilomyces, Eupenicillium*, and *Doratomyces*.

4. The food product according to claim 3, wherein the fermented soy ingredient is the product of fermentation of *Monascus*.

5. The food product according to claim 1, wherein the food product is a spread, meat product, baking good, beverage or bar.

6. The food product according to claim 1, wherein the food product is a bar, beverage or meat product.

7. The food product according to claim 6, wherein the food product is a meat product having the following composition: minced meat 60–80 wt %, mycoprotein 15–25 wt %, 2–10 wt % fermented soy protein comprising a statin, 0.1–1 wt % sodium caseinate, 0.1–1 wt % transglutaminase, nitrite salt 0.5–5 wt %, glucose 0.1–1 wt %, *Pediococcus* culture mix 0.001–0.010 wt % and 0–1 wt % optionally other ingredients.

8. Food product according to claim 6, wherein the food product is a meat product having composition: 10–40 wt % minced pork meat, 5–20 wt % minced beef meat, 2–10 wt % fermented soy protein comprising statin, 0–5 wt % salt, 0–5 wt % nitrite, 0–5 wt % phosphate, 20–50% water.

* * * * *